United States Patent
Maier et al.

(10) Patent No.: US 9,974,557 B2
(45) Date of Patent: May 22, 2018

(54) METHOD AND SYSTEM FOR CONTROLLABLE ADJUSTMENT OF THE REMOVAL RATE OF CUTTING EDGES OF EFFECTORS OF MANUALLY-GUIDED MATERIAL- AND TISSUE-SECTIONING TOOLS AND A CORRESPONDING EFFECTOR

(71) Applicant: ALL-OF-INNOVATION GmbH, Ismaning (DE)

(72) Inventors: Thomas Maier, München (DE); Sebastian Heininger, Haar (DE); Erik Loewe, Ainring (DE); Tim Lueth, Ismaning (DE)

(73) Assignee: ALL-OF-INNOVATION GmbH, Ismaning (DE)

( * ) Notice: Subject to any disclaimer, the term of this patent is extended or adjusted under 35 U.S.C. 154(b) by 434 days.

(21) Appl. No.: 14/571,564

(22) Filed: Dec. 16, 2014

(65) Prior Publication Data
US 2015/0164527 A1    Jun. 18, 2015

(30) Foreign Application Priority Data

Dec. 17, 2013 (DE) .................. 10 2013 226 197
Apr. 14, 2014 (DE) .................. 10 2014 105 311

(51) Int. Cl.
*A61B 17/32* (2006.01)
*A61B 17/14* (2006.01)
(Continued)

(52) U.S. Cl.
CPC .......... *A61B 17/32* (2013.01); *A61B 17/1617* (2013.01); *A61B 17/1626* (2013.01);
(Continued)

(58) Field of Classification Search
CPC ... A61B 17/14; A61B 17/32; A61B 17/32002; A61B 17/147; A61B 2017/320052;
(Continued)

(56) References Cited

U.S. PATENT DOCUMENTS 5,141,513 A * 8/1992 Fortune .............. A61B 17/1735
606/53
5,389,101 A * 2/1995 Heilbrun .................. A61B 5/06
348/E13.014

(Continued)

FOREIGN PATENT DOCUMENTS

DE           4401496 A1 *  8/1995  ....... B23B 29/03457
DE           19960020 A1    6/2001
(Continued)

OTHER PUBLICATIONS

Lueth, et al., "A Surgical Robot System for Maxillofacial Surgery," Proceedings of the 24th Annual Conference of the IEEE, vol. 4, pp. 2470-2475 (Sep. 1998).

*Primary Examiner* — George C Neurauter
(74) *Attorney, Agent, or Firm* — Ewers & Hasselmann PLLC

(57) ABSTRACT

Methods, systems and tools are provided for controllable adjustment of a removal rate of cutting edges of rapidly rotating effectors of manually-guided material- and tissue-separating tools without significantly changing the rotation speed of the effectors or the position, orientation or the geometry of the effectors, and in particular, for precisely maintaining work space boundaries during material and tissue removal with effectors in rapidly rotating machine tools in surgery and freehand manufacturing to produce free-form surfaces. The manually-guided material-separating and tissue-separating tools and effectors allow controllable adjustment of the removal rate of the material-separating cutting edges of the effector by mechanically (Continued)

adjusting a position or orientation of at least one cutting edge cover at a constant rotation speed of the effector without appreciable change of the removal movement.

14 Claims, 4 Drawing Sheets

(51) Int. Cl.
*A61B 17/16* (2006.01)
*A61B 34/20* (2016.01)
*B23C 1/20* (2006.01)
*B23C 5/24* (2006.01)
*B23Q 15/10* (2006.01)
*G05B 19/18* (2006.01)
*G05G 7/12* (2006.01)

(52) U.S. Cl.
CPC ............. *B23C 1/20* (2013.01); *B23C 5/2458* (2013.01); *B23C 5/2462* (2013.01); *B23Q 15/10* (2013.01); *G05B 19/182* (2013.01); *A61B 17/147* (2016.11); *A61B 17/32002* (2013.01); *A61B 34/20* (2016.02); *A61B 2017/320052* (2013.01); *A61B 2034/2051* (2016.02); *A61B 2034/2055* (2016.02); *G05G 7/12* (2013.01)

(58) Field of Classification Search
CPC .......... B23Q 15/10; G05B 19/18; G05G 7/12; G05G 2700/18; G05G 2009/04748
USPC ................. 604/165.01–165.04; 606/182–183
See application file for complete search history.

(56) References Cited

U.S. PATENT DOCUMENTS

| | | | | |
|---|---|---|---|---|
| 5,490,860 A * | 2/1996 | Middle | ............ | A61B 17/32002 604/22 |
| 6,562,055 B2 * | 5/2003 | Walen | ................ | A61B 17/1615 606/167 |
| 7,079,885 B2 * | 7/2006 | Marmulla | ............... | A61B 34/20 600/426 |
| 7,346,417 B2 * | 3/2008 | Luth | ....................... | A61B 34/20 128/920 |
| 7,422,582 B2 * | 9/2008 | Malackowski | .... | A61B 17/1613 606/1 |
| 7,725,162 B2 * | 5/2010 | Malackowski | ........ | A61B 90/36 600/424 |
| 7,950,306 B2 * | 5/2011 | Stuart | ....................... | B25J 9/106 74/490.01 |
| 8,366,674 B2 * | 2/2013 | Frassica | ............ | A61M 25/0017 600/101 |
| 8,961,536 B2 * | 2/2015 | Nikou | ................ | A61B 17/1622 606/130 |
| 9,480,485 B2 * | 11/2016 | Aho | .................... | A61B 17/1617 |
| 9,480,534 B2 * | 11/2016 | Bowling | .................. | B25J 13/00 |
| 9,566,121 B2 * | 2/2017 | Staunton | .......... | A61B 17/32002 |
| 2004/0208717 A1 * | 10/2004 | Greenhalgh | ........ | B23B 51/0018 408/224 |
| 2008/0208230 A1 * | 8/2008 | Chin | .................. | A61B 17/1617 606/167 |
| 2009/0270791 A1 * | 10/2009 | Todd | ................ | A61B 17/32002 604/22 |
| 2011/0190803 A1 * | 8/2011 | To | ....................... | A61B 17/1671 606/180 |
| 2011/0282373 A1 * | 11/2011 | Chekan | ................ | A61M 25/007 606/170 |
| 2011/0295272 A1 * | 12/2011 | Assell | .............. | A61B 17/32002 606/131 |
| 2012/0123418 A1 * | 5/2012 | Giurgi | .................... | A61B 17/16 606/80 |
| 2012/0143209 A1 * | 6/2012 | Brecheen | ................ | A61B 17/42 606/119 |
| 2014/0039517 A1 * | 2/2014 | Bowling | .................. | B25J 13/00 606/130 |
| 2014/0276202 A1 * | 9/2014 | Polster | ............... | A61B 10/0266 600/564 |
| 2014/0288560 A1 * | 9/2014 | Rubin | .............. | A61B 17/32002 606/79 |
| 2017/0079710 A1 * | 3/2017 | Deville | .............. | A61B 18/1445 |
| 2017/0095268 A1 * | 4/2017 | Schneider | ...... | A61B 17/320758 |

FOREIGN PATENT DOCUMENTS

| | | |
|---|---|---|
| DE | 102009057434 A1 | 6/2011 |
| EP | 1346694 A2 | 9/2003 |
| WO | 02076302 A2 | 10/2002 |

* cited by examiner

METHOD AND SYSTEM FOR CONTROLLABLE ADJUSTMENT OF THE REMOVAL RATE OF CUTTING EDGES OF EFFECTORS OF MANUALLY-GUIDED MATERIAL- AND TISSUE-SECTIONING TOOLS AND A CORRESPONDING EFFECTOR

CROSS REFERENCE TO RELATED APPLICATIONS

This application claims foreign priority to German Application No. DE 102014105311.7 filed on Apr. 14, 2014 and to German Application No. DE 102013226197.7 filed on Dec. 17, 2013, the entire contents of which are hereby incorporated by reference.

FIELD OF THE INVENTION

The disclosure relates to a method and a system for controllable adjustment of a removal rate of manually-guided material- and tissue-sectioning tools with effectors, and to a corresponding effector.

BACKGROUND

Methods, systems and tools with effectors are useful in particular for the precise adherence to work space boundaries during material and tissue removal with tools of rapidly rotating machine tools in surgery and in hand-crafting of free-form surfaces.

When hand-crafting in repair shops and in interventional medical treatment of humans and animals, manually-guided and manually-guided tools in form of driven machine tools (for example drill press with a drill or a milling tool, electrical planer) are frequently used for separating and removing material and tissue of an object. This is typically used, in addition to free-form shaping, for the spatial adaptation the object surface to a precisely fitting counterpart with defined boundaries. At the same time, certain structures or surfaces of the object must not be harmed with the tool, for example to protect an already finish-machined surface or structures inside the object, which are hidden from the view of the user.

To date, the following methods are known in the related art as technical aids for manually-guided and manually-positioned tools:

a) Navigation methods which measure the position and orientation of tools relative to object and graphically and acoustically indicate to the user the position, orientation and distance of the manually-guided tool to the allowed work space boundaries relative to object (Surgical Navigation, U.S. Pat. No. 5,389,101, DE 19960020) as well as graphically indicate the areas on the object that still need to be machined.

b) Template attached to the object for limiting the free movement of the manually-guided tool within the allowed work space boundaries relative to the object (Ancient Times, Middle Ages, Surgical Template U.S. Pat. No. 5,141,513).

c) Compliant mechanisms and robots, to which the manually-guided tool is attached. These mechanisms and robots change, relative to the allowed work space boundaries, the freedom, friction, stiffness and elasticity of the manually-guided movement on the object and apply even forces and torques in addition to the manual guidance (Lueth, T. C. et al., "A surgical robot system for maxillofacial surgery," Industrial Electronics Society, 1998th IECON '98. Proceedings of the 24th Annual Conference of the IEEE, vol. 4, no., pp. 2470-2475).

d) Limiting the position, orientation, distance and signal-based removal rate relative to the object or structures of the object (Navigated Control, DE 000010117403C2).

e) Mechanisms for linearly deploying and retracting a rotating effector relative to a protective sleeve surrounding the effector (Blue Belt Technologies, US 2012/0123418A1) for limiting the removal rate.

Methods for adjusting of tool cutting edges are known from the published documents (DE 4401 496 A1), however not for handheld or manually-guided machine tools, whose movements of the tool position and the tool orientation cannot be definitely specified in advance by a program. No method is known that allows adjustment of the tool cutting edges without coupling to a programmable motion control. Likewise, no method is known that allows a computer-controlled or position-based adjustment of a rotating tool of a handheld or manually-guided machine tool.

A method to extend the cutting edges subsequent to wear of the cutting edges is known from EP 0977644B1.

With reference to the application of manually-guided driven tools with effectors in surgery, extensive experience has been gained over the last 20 years due to the increasing demand for efficiently fitting medical implants (e.g. knee, hip and the like). The disadvantages are similar to those encountered in hand-crafting of materials. The disadvantages of the present art are as follows:

a) Pure navigation methods with graphic, acoustic and tactile, vibrating feedback do not solve the problem, that the user inadvertently misaligns the material-removing tool due to a slip or lack of concentration and thus violates work space boundaries. The less time is available for learning and executing the applications, the greater is the risk. The risk increases when the material has different densities, the tool is deflected or the user works in an unergonomic posture and is subjected to shocks or forces.

b) Templates attached to the object require a sufficiently large available surface for attaching the template. In addition, templates exhibit their advantage primarily when the tool is inserted into the template in a preferred direction. It is currently not possible to mill a three-dimensional free-form surface while at the same time enabling three-dimensional mobility and three-dimensional orientation of the tools. Three-dimensional free-form surfaces can only be produced at great expense. Templates that cannot clearly be form-fittingly applied require navigation methods for aligning and affixing the templates to the object. Templates always require additional space on the object.

c) Compliant (compliant motion, hands-on) robots, on which the manually-guided instrument is attached, have a limited working space and must be aligned relative to the object prior to use in a complex process. During operation, hands-on robots allow a seemingly free movement of the instrument. The high inertia of the robot in relation to the manually-guided tool or object are a limiting factor for the precise adherence to work space boundaries even with optimal dynamic control of a highly dynamic drive. Robots are also expensive to procure and operate, require a dedicated space next the object, and have a large mass. They also must be covered under sterile working conditions.

d) Although the method for position-, orientation-, distance-, and signal-based control of the removal rate (navigated control) is indeed optimally suitable for adhering to the work space boundaries, a dynamically controllable change of the removal rate is still a prerequisite in order to compete in terms of time with a template or a mechanisms/robotic solution in the boundary area. Likewise, precise adherence to the work space boundaries can only be achieved when the removal rate of the tool has the steepest possible transition. Shutting off the power is currently problematic with pneumatic or electric drives due to the high mass inertia of the tool, because the force applied to the hand changes strongly during the switching operation.

e) The mechanism for reducing the removal rate by relative movement of a protective sleeve disposed around the effector makes it possible to limit the removal rate while keeping the rotation speed constant. However, because the protective sleeve is larger than the effector itself and can be blocked by the object surface, often only a fast retraction or deflection of the tool is possible in practice. Masses are here also moved. In addition, the relative movement must be compensated earlier or later by hand, which prevents a fast operation with high precision.

SUMMARY

It is an object of an exemplary embodiment to obviate the known disadvantages of the prior art and to develop a method, a system and an effector for an tool, which makes it possible to control the removal rate of rapidly rotating tools, without the need to significantly change the rotation speed of tool or its the position, orientation or the geometry of the tool with the effector.

The disclosed system has the particular advantage that no jerk or shock is imparted on the hand that guides the tool with the effector, because the material-separating cutting edges of the tool can be mechanically adjusted in their location (position and orientation) relative to tool effector in at least two positions or can be deployed or retracted at a constant or only slightly changed rotation speed of the effector. This makes it possible to work manually quickly and with high precision. It is also possible to mechanically adjust, or deploy or retract, at least one cover of the cutting edge disposed forward of the material-separating cutting edges of the tool in its location (position and orientation) relative to tool effector in at least two positions in order to adjust the removal rate of the material-separating cutting edges of the tool. It is hereby possible to limit the removal rate of the effector of the tool depending on the direction in order to hereby force a preferred direction or a preferred volume during material removal, because the tool can remove material and further penetrate into the object only in the unblocked preferred removal direction.

The system can be readily and inexpensively produced, reliably applied and readily serviced, because the removal direction set on the tool is easily visually discernable on the tool for the user (for example, by coloring the cutting edges) or is acoustically or graphically signaled (for example, via a display on a display screen).

The change in the removal rate takes place in less than 1/10 second.

According to an aspect of an exemplary embodiment, the removal rate is controlled based on a continuously measured position of the manually-positioned or manually-guided tool and optionally based on mathematical derivatives of the position as well as based on spatial relations to defined boundaries relative to the material or tissue to be removed or to an object body measuring marker, wherein the removal rate is controlled based on a sensor signal or control signal.

According to another aspect of an exemplary embodiment, the position and orientation of the effector due to an adjustment of the cutting edges or cutting edge cover does not change at all or only in the order of magnitude of the cutting edge length of the cutting edges and the spatial extent of the effector due to the adjustment of the cutting edges or cutting edge does not change at all or only in the order of magnitude of the cutting edge length or the cutting edge cover. The adjustment of the removal rate hence does not require a correction of the position or orientation of the effector. The modified removal rate is attained with an unchanged position of the effector.

Furthermore, it is advantageous to obtain the required energy for maintaining the signal connection and to control of the actuator directly from the kinetic energy or from the drive of the tool movement. It is also advantageous if the cutting edges and/or the cutting edge covers are pressed outwardly by an internal stator by way of at least one adjustable actuating lamella so as to uncover only a portion of the cutting edges for material removal and to thereby limit the removal direction relative to the location of the stator (or of the tool measuring marker), wherein the position of the stator relative to the tool measuring marker is known and the removal rate of the effector is directionally controlled by an adjustment.

The method and system can advantageously be used, in particular, for precise adherence to work space boundaries during material and tissue removal with tools in rapidly rotating machine tools in surgery and in free-hand manufacturing for producing free-form surfaces. The change in the removal rate at constant rotation speed and effector position enable a very rapid manual tool movement, for example cross-hatched back and forth movements, with precise removal boundaries as well as automatic centering and direction correction of the manually-guided effector and hence also of the tool.

The method and a corresponding system as well as a tool are another elementary step for increasing the precise processing power of a person by way of his motor skills in combination with a signal-, position-, orientation-, and distance-based fast reduction of the removal rate of a tool that is manually guided by this person.

Several tools with lower removal rate can be emulated by adjusting the cutting edges, thereby reducing the number the tool changes. Instead of using effectors with shorter cutting edge lengths, the effective cutting edge lengths can be reduced for the surface finish. The surface quality improves.

The range of applications of rotating tools will increase again at the expense of other separating methods, like lasers, because the removal rate can be adjusted with similar speed and significantly faster than until now. This enables the application of manually-guided tools, which for functional reasons have mass inertia or which can be undesirably deflected due to the interaction between tool and material, for precision tasks.

The range of applications of handheld and manually-guided machine tools will thus significantly increase because a person can provide services similar to a machine tool. Accordingly, more people can perform more demanding activities, which so far has only been accomplished by machine tools. Furthermore, the spectrum of manual activities demanding precise three-dimensional surface machining will increase.

With respect to applications in bone surgery, the accuracy of tight fits of orthopedic implants will be significantly improved, i.e. smaller interventions can be carried out with higher precision. The speed with which orthopedic implants are fitted (preparation and fitting) will increase significantly. The reduction in time has a positive effect on the healing process of the patients. The growing number of particularly older people with increasing demand for replacement of knee, hip and shoulder joints will be satisfied with a constant or decreasing number of surgeons.

The costs for the acquisition of durable goods (medical robots) for achieving high implantation rates will decrease substantially. Presently, automated implantation processes are an essential prerequisite to ensure that the necessary joint replacement surgery due to the aging society can be performed with a constant or decreasing number of surgeons.

BRIEF DESCRIPTION OF THE DRAWINGS

Exemplary embodiments will now be described with reference to the drawings.

DESCRIPTION OF EXEMPLARY EMBODIMENTS

Figure 1:
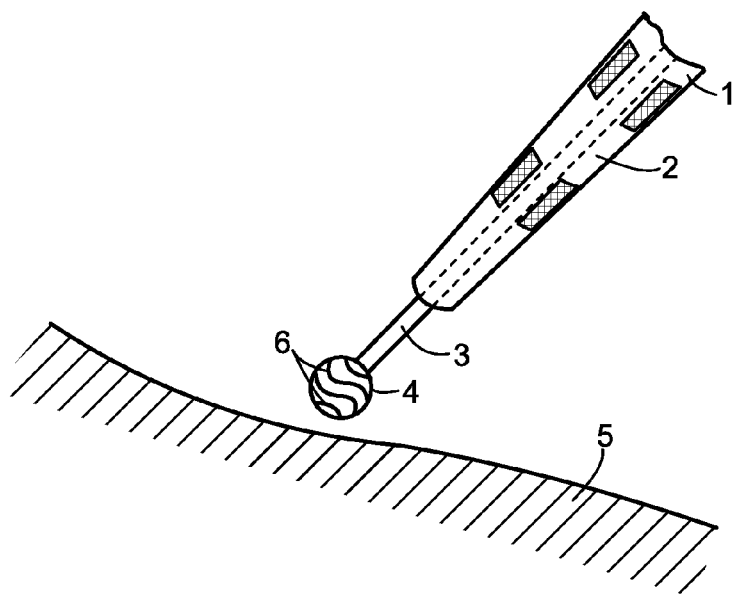
FIG. 1 is a schematic view illustrating a handheld tool with a rotating material-separating effector according to an exemplary embodiment.

FIG. 1 shows a manually-guided power tool 1 of a type used for material separation and/or chip-removing machining such as drilling, milling, sawing, separating and so on. Pneumatic or electric drives are frequently used when high rotation speeds must be achieved for attaining the necessary removal rate according to an exemplary embodiment. The tool 1 transfers the torque for material separation typically by way of a rigid or flexible shaft 3 by which the material separating tool 1 is connected to the actual tool effector 4 by way of a chuck 2. The rotating effector 4 which is matched to the cutting speed is placed on the material 5 or the tissue 5. The cutting edges 6 on the effector 4 hereby cut the material 5 open and remove part of the material 5.

Figure 2:
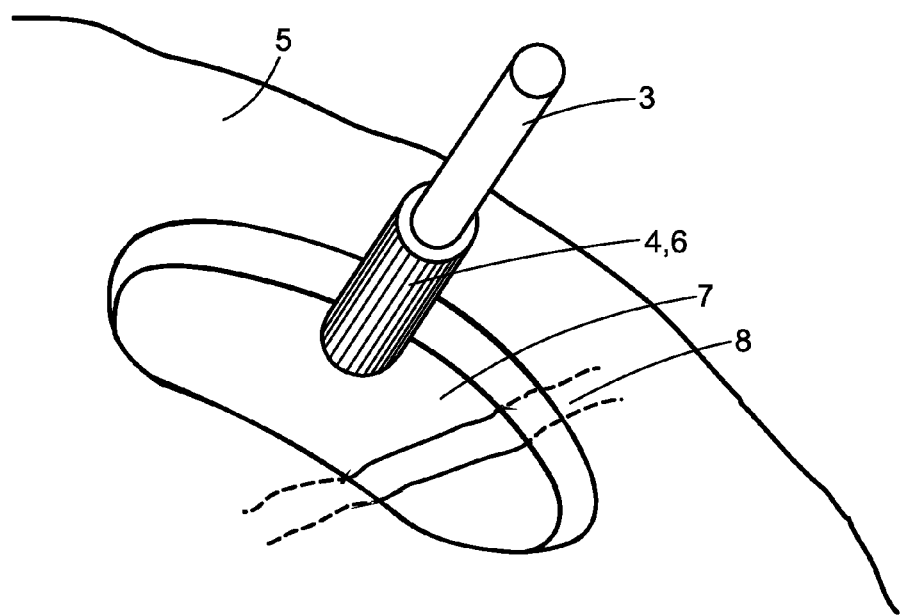
FIG. 2 is a schematic view illustrating a dimensionally stable and positionally accurate cavity to be milled in an object with a sensitive structure hidden underneath according to an exemplary embodiment.

FIG. 2 shows a surface structure into which a precisely fitting cavity 7 is to be milled, without inadvertently damaging a sensitive structure 8 located in the material 5 with the effector 4 embodied as a milling effector according to an exemplary embodiment. The removal rate of the tool 1 and of the effector 4 may be reduced at the planned boundary of the cavity 7 and proximate to the structure 8 to be protected by adjusting the cutting edges 6, without the need to reduce the rotation speed of the tool 1. At most, the rotation speed is slightly reduced. In this way, the change in the rotation speed of the rotating masses of motor and tool 1 does not impart a jerk or shock on the hand holding the tool 1.

Figure 3:
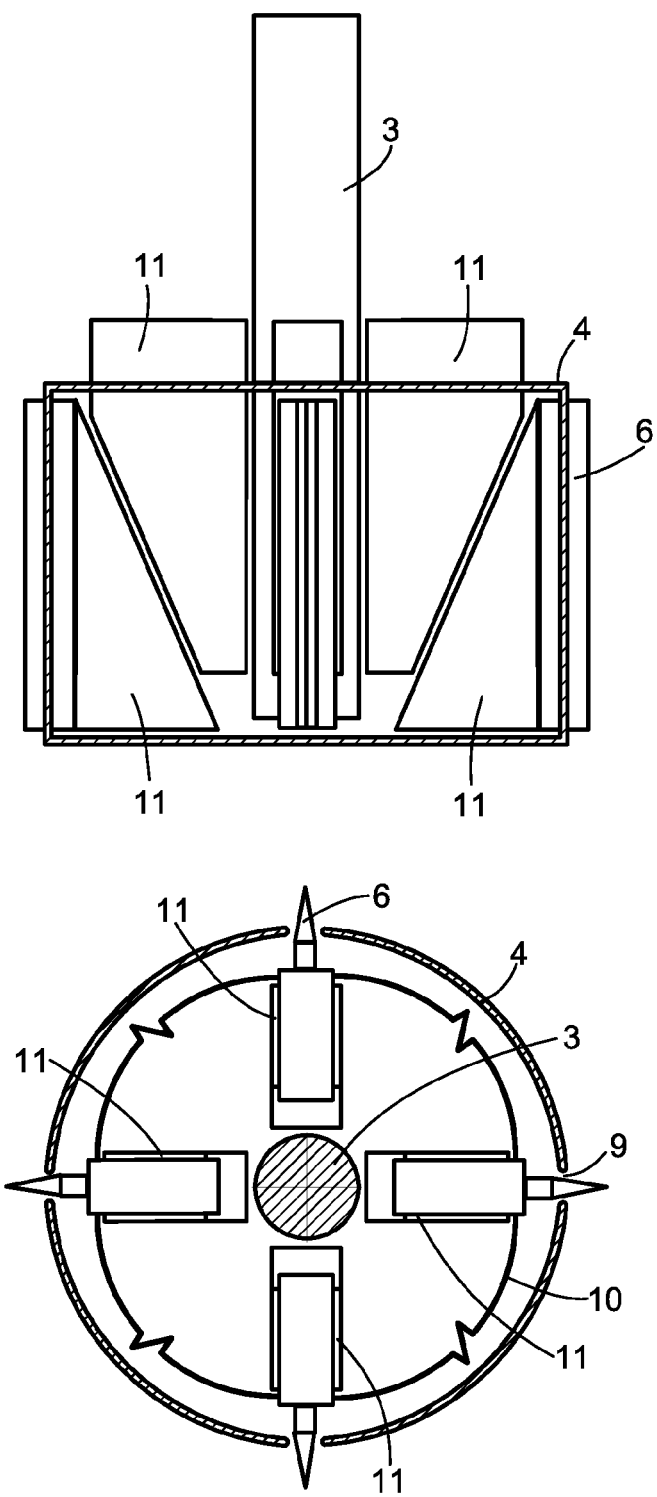
FIG. 3 is a block diagram of a material-separating effector with tool edges that can be retracted and deployed at a high rotation speed according to an exemplary embodiment.

FIG. 3 is a side view and a view from below of the material-separating tool 1 with the shaft 3, the effector head of the effector 4 and the adjustable cutting edges 6 according to an exemplary embodiment. The figure shows four cutting edges 6, which can be pushed out and retracted through openings 9 of the effector head of the effector 4. The openings 9 for deploying the cutting edges 6 are designed, so that the cutting edges 6—when retracted—are unable to remove any material or only an insignificant amount of material even at high rotation speed and with direct contact between the effector 4 and the surface of the material or tissue 5 to be removed. FIG. 3 shows the openings 9 with rounded edges. A retraction mechanism 10 ensures that the cutting edges 6 themselves do not unintentionally cause a material separating effect even at high rotation speed and upon contact, but retract behind the openings 9 for protection. The retraction mechanism 10 in FIG. 3 is embodied by spring elements connecting the cutting edges.

To push the cutting edges 6 from the protective position, a deployment mechanism 11 is required. This deployment mechanism 11 is designed in FIG. 3 as a wedge mechanism, which when depressed exerts a radially acting force on the cutting edges 6, pressing them outwardly into engagement with the material. All elements shown in FIG. 3 rotate as part of the effector head of the effector 4.

Figure 4:
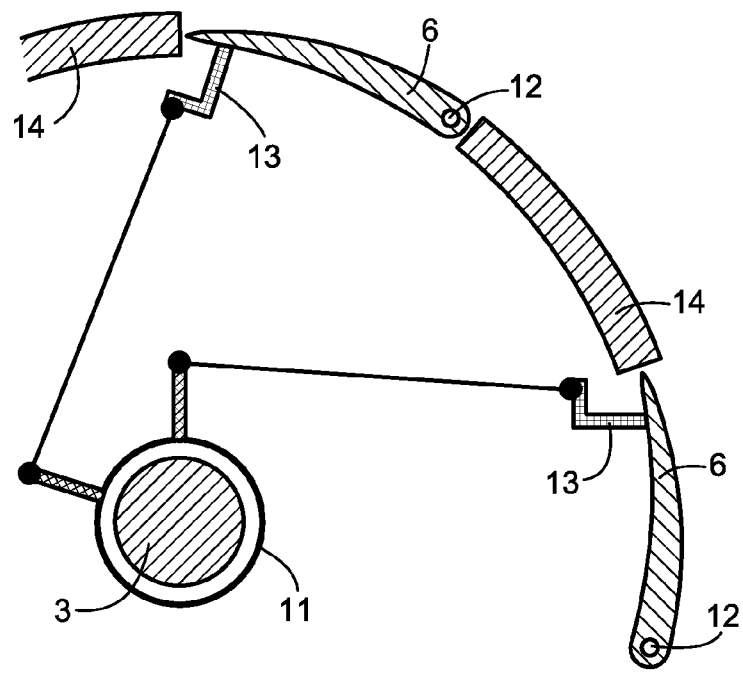
FIG. 4 is a block diagram view of a cross section through a material-separating effector, illustrating how the cutting edges can be adjusted via articulated joints according to an exemplary embodiment.

FIG. 4 shows another exemplary embodiment of the tool 1 in which the cutting edges 6 are not retracted, but are instead mounted on the outer surface of the effector 4 with swivel joints 12. They can be deployed by applying pressure from the inside to the outside. Preferably, a stop 13 suitably prevents the cutting edges 6 from breaking out. The swivel joints 12 are preferably implemented as flexure joints which can be generated by suitable weakening and/or shaping of the material. The mechanism of the cutting edges 6 is shown here in cross section; however, all elements may extend around a cylindrical core in form of a stretched spiral (helix) similar to a drill bit.

The deployment mechanism 11 in FIG. 4 is not implemented as a wedge, but instead as an articulated joint, and twisting of the deployment mechanism 11 with respect to the shaft 3 causes the cutting edges 6 to be pulled out beyond the cutting edge protection 14. The deployment mechanism may also be twisted by a helical linear movement.

Figure 5:
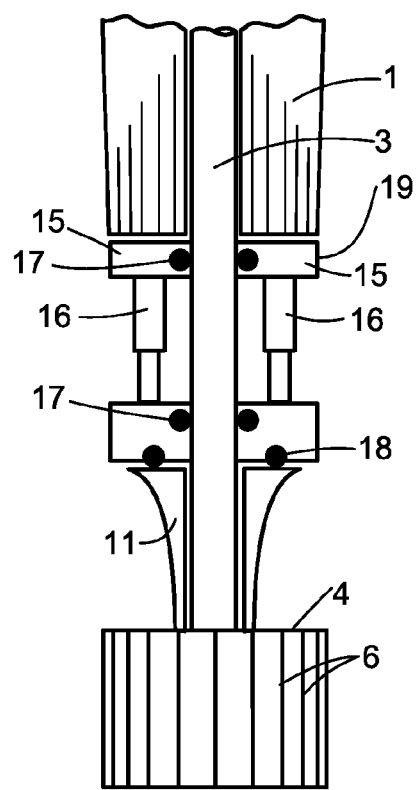
FIG. 5 is a block diagram illustrating a transfer of the actuating forces for adjustment of the cutting edges while the tool rotates with the removal rate according to an exemplary embodiment.

FIG. 5 shows an exemplary embodiment in which actuating forces are transferred for adjusting the cutting edges 6 by way of a cutting edge control attachment 15. The cutting edge control attachment 15 is connected for this purpose either directly with the hand piece of the tool 1 or it is clamped together with the shaft 3 and the cutting edge deployment mechanism 11 with the chuck 2 during the clamping process. A bearing or support 17 is advantageously arranged to decouple the movement of the cutting edge control attachment 15 from the movement of the tool. A bearing or support 18 is also advantageous for decoupling the cutting edge actuating movement from the tool movement and the cutting edge deployment mechanism 11. The actual adjusting movement is achieved with an actuator 16 which is designed in FIG. 5 as a linear motor, for example a piezoelectric motor, but which may also be designed for pneumatic, hydraulic or electrodynamic operation.

The cutting edge deployment mechanism 11 could also be pulled by another bearing, which is not illustrated in FIG. 5. The actuator 16 would then also be able to adjust the cutting edge position in both directions without requiring a separately constructed passive retraction mechanism 10.

Figure 6:
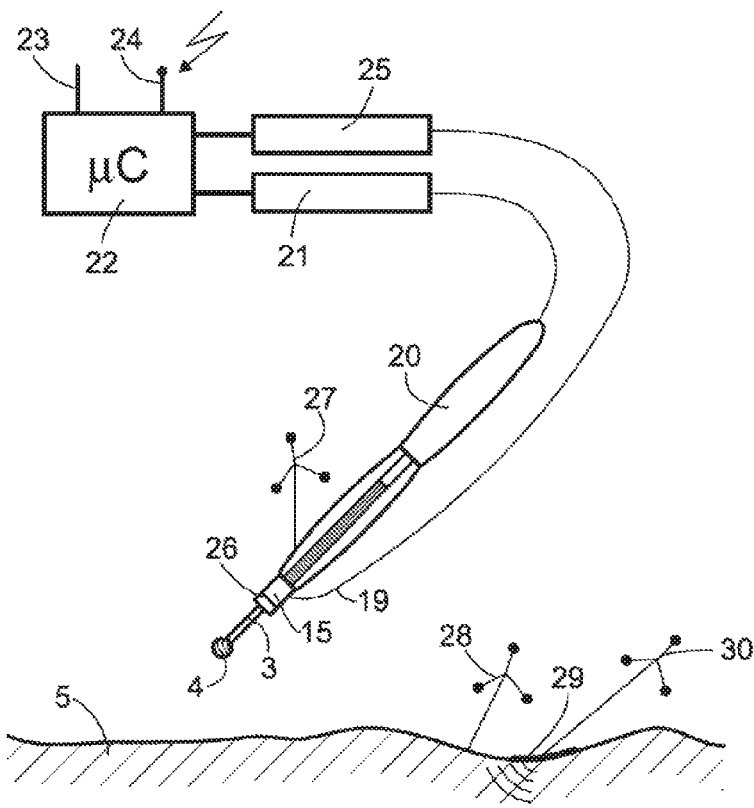
FIG. 6 is a schematic view illustrating a signal-, position-, orientation- and distance-dependent control of the tool cutting edges in relation to the machined material or tissue according to an exemplary embodiment.

FIG. 6 shows machine drive 20, which can be controlled via a power amplifier and/or a motor controller 21 by signals from a control computer 22 according to an exemplary embodiment. The speed settings of the control computer 22 are received via an external signal line 23 or a signal radio link 24, in order to be able to control for example the rotation speed of the machine with a foot pedal (not shown). Likewise, a cutting edge adjusting control 25 of the actuator serves to adjust the cutting edge via the control signal line 19. It is also possible to signal via the signal line 23 or the signal radio link 24 the immediate adjustment of the cutting edges 6, for example when the effector 4 leaves the boundaries of the work space. For measuring the position and orientation of the tool 1, it is known to affix relative to the tool 1 or the machine a measuring marker 27 for a coordinate measuring system (not shown). A second measuring marker 28 is affixed on the material or tissue 5 to be removed of the object to be processed. The resulting information about the relative movement and the boundary of the work space is either processed externally or transmitted to the control computer 22, from where the rotation speed or the position of the cutting edge is then controlled. The measuring markers 27, 28, 30 are in FIG. 6 designed as reflectors for an optical coordinate measuring systems. However, these could also be measuring markers for an electromagnetic coordinate measuring system. In this case, a rotation speed sensor 26 is preferably mounted on the tool 1 in order to receive the frequency of the electromagnetic interference fields at the place of origin and to forward these to the control computer 22 and the coordinate measuring system, where they are filtered out by a band stop filter. Instead of a position-based adjustment of the cutting edges 6 relative to work space boundaries, direct image signal processing of a signaling or imaging system for generating the cutting edge adjustment is also possible. For this purpose, a signaling or imaging system 29, for example a nerve monitor or a multidimensional imaging device is used to capture the signals. It can then be directly recognized in the signal or image whether the cutting edges 6 need to be switched.

Figure 7:
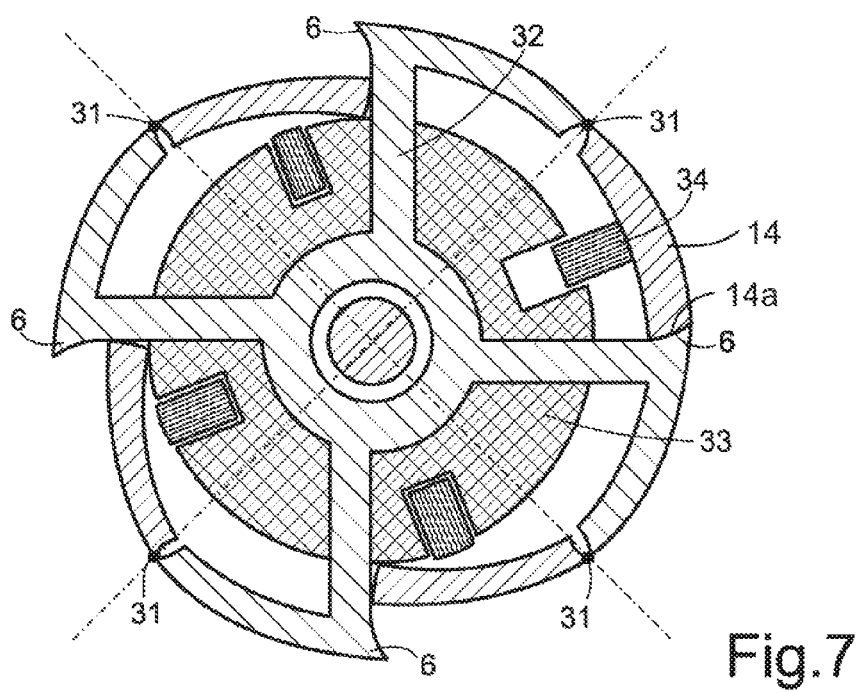
FIG. 7 is a block diagram of a cross section through a material-separating effector illustrating how the removal rate of the cutting edges can be reduced by cutting edge covers according to an exemplary embodiment.

FIG. 7 shows another exemplary embodiment in which—in the context of material removal—not the cutting edge 6, but a cutting edge protection 14 with a cutting edge cover region 14a is adjusted by way of an articulated cutting edge cover joint 31 constructed as a swivel joint or flexure joint is adjusted with respect to the cutting edge 6. If needed, the opening between the cutting edge protection 14 and the cutting edge 6 closed. When using other—unillustrated—flexure joints between the cutting edge protection 14 and the cutting edge 6, the surface of the effector 4 may be designed to be completely closed in order to prevent particles from entering the effector 4. In FIG. 7 the cutting edges 6 are fixedly and non-adjustably attached on a hollow shaft 32 which rotates with the cutting speed about a centered stator 33 and is preferably supported at two locations in an annular manner. The orientation of the stator 33 relative to the tool 1 or to the tool measuring marker 27 is known. The cutting edge protection 14 is attached directly to the rear of the cutting edge 6 by way of its cutting edge cover joint 31. In the deployed state, the cutting edge cover region 14a covers the cutting edge 6 and also presses during the deployment movement material residues disposed in front of the cutting edge 6 outward. Without inside pressure, the radius-following shaping causes the cover to be pressed into the effector 4, thereby exposing the cutting edges 6. At least one adjustable actuating lamella 34 is disposed in a recess in the stator 33, which can be deployed and retracted from the rotationally symmetric shape of the stator 33 in at least one direction. Other variants for changing the radius of the stator 33 in at least one location are feasible. By deploying the actuating lamellae 34 on the stator 33, the tool 1 loses its removal effect in this direction. When the lamellae 34 are adjusted in all directions, the entire effector 4 will lose its removal rate. When the lamellae 34 are retracted in a deliberate manner, then the effector 4 assumes relative to the tool 1 or the tool measuring marker 27 an adjustable removal rate limited by the orientation. The removal rate of the effector 4 can then be limited to specific angular segments by suitable control with the control computer 22. The actuating lamellae 34 can not only be moved electrically, but also hydraulically or pneumatically. The latter is particularly advantageous for pneumatic drives.

The method allows reducing the removal rate of at least one of the material-removing cutting edges 6 of a manually-guided tool 1 by an adjustment movement of the cutting edges 6 or of a cutting edge protection 14. In this manner, the removal rate of the material-removing effector 4 on the object can be adjusted and reduced with a uniform tool movement. By maintaining the uniform tool movement and a constant rotation speed, only minimal forces or torques are imparted on the hand guiding the tool. The removal rates can be changed very quickly due to the short adjustment paths.

A distinction is made, on the one hand, between signal-based control and, on the other hand, control of the removal rate in dependence of the tool pose (position and orientation).

The following is an exemplary embodiment of the signal-based control: when drilling a hole with an electric drill in a wall of a room, it may be detected by a signaling sensor that an electrical line or a water pipe is located in the direction of the drilling channel which should not be damaged by the drill. In this situation, the removal rate of the drilling tool is immediately reduced, so that the lines are not damaged.

According to another aspect of an exemplary embodiment: when drilling a cavity in the mastoid region of the cranial bone, it is detected by a signaling sensor that a neural pathway or a blood vessel extends through the bone in the direction or in close proximity of the drilling channel which should not be damaged by the drill. In this situation, the removal rate of the drilling tool is immediately reduced, so that the pathway and blood vessel, respectively, are not damaged.

Both embodiments are intended to serve as safety measures which do not require spatial preplanning by the operator/doctor, but where a switching signal is transmitted by an integrated sensor or an external sensor. Under these circumstances, it may in principle be useful to manually increase the removal rate in order to realize a cost-effective tool 1, while a shutdown is then signal-based.

In other situations, it is advantageous to allow a startup operation by way of a signal. In this case, the tool 1 would already be located at exactly the correct position with the correct rotation speed when the removal rate is switched in. The known problem associated with torque transmission via static friction and the resulting change in position with insufficient manual holding force is then eliminated.

An exemplary embodiment of the pose-based control of the tool similar to the performance control from (U.S. Pat. No. 7,346,417) is the following: For introducing an implant support in form of a cavity into a femur for an artificial knee joint, it is necessary to mill a free-form surface into the bone at a specific position and orientation on the bone. Both the access opening and the working angle are hereby severely limited. As soon as the effector 4 of the manually-guided freehand tool 1 is located at the boundary of the allowed work space, the removal rate of the effector 4 is reduced by adjusting the cutting edges 6 or the cutting edge cover 14 without reducing the machine tool power. Because of the largely constant mass inertia due to the constant rotation speed of the machine tool and of the effector 4 of the tool 1, the removal rate can be abruptly changed at the boundary of the allowed work space, without imparting significant force or torque impulses (jerk) on the guiding or positioning hand. As an alternative to an abrupt change in the removal rate, it may be advantageous to adjust the removal rate relative to the distance to the work space boundary in several steps or continuously, in order to achieve a high surface finish at the boundary surfaces.

The following is another exemplary embodiment of the tool-position-based control in conjunction with a direction-controlled removal rate: when drilling a hole with an electric drill in a wall of a room, it may be detected by a continuous position measurement (position/orientation) that the drill is located close to the planned drilling position. In this situation, the removal rate is reduced depending on the direction, so that material is removed only in the direction of the planned drilling position. The drill then slides automatically to the planned drilling position.

The advantages of power control manually-guided freehand machine tools based on position, orientation and distance data has been extensively disclosed in U.S. Pat. No. 7,346,417, so that the applications will not be cited here again. Likewise, coupling of the power control with direct measurement data from nerve monitoring, i.e. the reduction of the removal rate based on effects measured directly on the object with sensors (here a patient's body), which are based on processing of the object, is known.

The adjustment of the removal rate, limited to a reduced number of the cutting edges 6, is advantageous employed when material 5 needs to be removed in narrow working channels in only one direction, for example to produce grooves. The tool 1 then separates the material only in the preset direction.

It is not always obvious to the operator or the surgeon where and in which direction material 5 must still be removed. It is here advantageous when the effective removal rate as a function of the direction can be visually perceived. This can be achieved, for example, by a clearly recognizable coloring of the cutting surfaces the cutting edges 6. The user then sees the coloring always in those directions where a removal rate can be achieved, even when the effector 4 of the tool 1 rotates very fast. It may be useful to install a similar mechanism on the shank of the tool 1 in order to render visible blunt or rounded surfaces instead of the cutting edges 6, which are preferably released by the same mechanism, in order to emphasize the working direction.

It is also known that the position information can not only be calculated based on the evaluation of markers (U.S. Pat. No. 5,389,101), but also directly based on the evaluation of object geometries (U.S. Pat. No. 7,079,885).

It can be advantageous, not only with pneumatic drives, to produce the energy for adjusting the removal rate and for controlling the removal rate directly from the drive power of the tool 1 by electrodynamic means.

What is claimed is:

1. A method for signal-based or position-based control of a removal rate of material-separating cutting edges of a manually-positioned or manually-guided material separating tool, the manually-positioned or manually-guided material separating tool including an effector and a shaft, the effector including the material-separating cutting edges and at least one cutting edge cover disposed on the material-separating cutting edges, the method comprising:
   controlling the removal rate of the material-separating cutting edges of the effector by:
      (a) mechanically adjusting at least two positions of at least one of the material-separating cutting edges or the at least one cutting edge cover disposed on the material-separating cutting edges in a radial direction relative to the shaft, the at least two positions including locations and orientations of the material-separating cutting edges or of the at least one cutting edge cover; or
      (b) retracting and deploying at least one of the material-separating cutting edges in the radial direction relative to the shaft; and
   maintaining or only insignificantly changing a rotation speed of the effector:
      (i) when the at least two positions of the at least one of the material-separating cutting edges or the at least one cutting edge cover are adjusted, or
      (ii) when the at least one of the material-separating cutting edges are retracted and deployed;
   the method further comprising least one of:
      maintaining a position and an orientation of the effector or changing the position and the orientation of the effector only in an order of a magnitude of a cutting length of the material-separating cutting edges when the material-separating cutting edges or the at least one cutting edge cover are mechanically adjusted, and
      maintaining a spatial extent of the effector or changing the spatial extend of the effector only in the order of the magnitude of the cutting length of the material-separating cutting edges or in an order of a magnitude of a length of the at least one cutting edge cover when the material-separating cutting edges or the at least one cutting edge cover are mechanically adjusted.

2. The method according to claim 1, further comprising:
   continuously measuring a position of the manually-positioned or manually-guided tool; and
   controlling the removal rate of the material-separating cutting edges based on the continuously measured position of the manually-positioned or manually-guided tool.

3. The method according to claim 1, wherein energy required to maintain a signal connection for the signal-based control of the removal rate and to control an actuator is obtained directly from kinetic energy or from a drive of a movement of the manually-positioned or manually-guided material separating tool.

4. The method according to claim 1, further comprising:
   pressing the material-separating cutting edges and the at least one cutting edge cover that rotate with a removal speed outwardly by an internal stator by way of at least one adjustable actuating lamella, so as to only release a subset of the material-separating cutting edges for removal and to limit a movement of the manually-positioned or manually-guided material separating tool to a movement in a removal direction relative to a location of the internal stator or of the tool measuring marker,
   determining a position of the internal stator relative to the tool measuring marker, and
   controlling the removal rate of the material-separating cutting edges of the effector as a function of the removal direction by the mechanically adjusting of the at least two positions of the at least one of the material-separating cutting edges and the at least one cutting edge cover.

5. The method according to claim 1, further comprising: visually, acoustically or graphically signaling a setting of a removal direction of the effector on the manually-positioned or manually-guided material separating tool.

6. The method according to claim 1, further comprising: calculating an optimal removal direction for a material processing to be performed by a calculation rule, and automatically setting the optimal removal direction for the material processing.

7. The method according to claim 1, further comprising: calculating a disturbance by an electromagnetic coordinate measuring system based on data obtained from a rotation speed sensor and including the disturbance in a position measurement.

8. A system for signal-based or position-based control of a removal rate of material-separating cutting edges of a manually-positioned or manually-guided material separating tool, the system comprising:
an effector including the material-separating cutting edges and a shaft, the material-separating cutting edges being configured to be mechanically adjustable in at least two positions in a radial direction relative to the shaft of the effector to control the removal rate of the material-separating cutting edges, the at least two positions including locations and orientations of the material-separating cutting edges,
wherein the effector is configured to at least one of:
maintain a position and an orientation of the effector or change the position and the orientation of the effector only in an order of a magnitude of a cutting length of the material-separating cutting edges when the material-separating cutting edges are mechanically adjusted, and
maintain a spatial extent of the effector or change the spatial extend of the effector only in the order of the magnitude of the cutting length of the material-separating cutting edges when the material-separating cutting edges are mechanically adjusted.

9. The system according to claim 8, wherein the effector includes at least one of a deployment mechanism, a retraction mechanism, and at least one cutting edge cover arranged on the material-separating cutting edges, and the at least one cutting edge cover being configured to be mechanically adjustable in the at least two positions relative to the effector to change the removal rate of the material-separating cutting edges.

10. The system according to claim 8, further comprising:
a cutting edge control attachment;
a control computer;
a rotation speed sensor; and
measuring markers.

11. An effector for a manually-guided tool, comprising:
a shaft; and
material-separating cutting edges, wherein the cutting edges are deployable and retractable by a cutting edge deployment mechanism and a cutting edge retraction mechanism in a radial direction relative to the shaft,
wherein the cutting edge deployment mechanism includes a two-piece wedge structure directly connected with the cutting edges or swivel joints by which the material-separating cutting edges are mounted on an outer surface of the effector, and
wherein the cutting edge deployment mechanism is operated by the two-piece wedge structure or by twisting the cutting edge deployment mechanism.

12. The effector according to claim 11, wherein the cutting edge retraction mechanism is operated by spring elements connected to the cutting edges.

13. The effector according to claim 11, further comprising:
cutting edge covers,
wherein the shaft is a hollow shaft and the cutting edges are immovably affixed to the hollow shaft, and the cutting edge covers are configured to be adjustable in the radial direction relative to the material-separating cutting edges.

14. The effector according to claim 11, further comprising cutting edge covers and actuating lamellae, wherein:
the material-separating cutting edges are connected with the cutting edge covers by cutting edge cover joints, and
the actuating lamellae are configured to adjust positions of the cutting edge covers.

* * * * *